United States Patent [19]

Soldati

[11] Patent Number: 4,673,570

[45] Date of Patent: Jun. 16, 1987

[54] GELLED ANTIPERSPIRANT COMPOSITIONS

[75] Inventor: Gianluigi Soldati, Mercerville, N.J.

[73] Assignee: Carter-Wallace, Inc., New York, N.Y.

[21] Appl. No.: 713,933

[22] Filed: Mar. 20, 1985

[51] Int. Cl.$^4$ .......................... A61K 7/34; A61K 7/38
[52] U.S. Cl. ......................................... 424/66; 424/68
[58] Field of Search .................................. 424/66, 68

[56] References Cited

U.S. PATENT DOCUMENTS 4,435,382  3/1984  Shin et al. .............................. 424/66

FOREIGN PATENT DOCUMENTS

| 1115213 | 12/1981 | Canada | 424/66 |
| 1164347 | 3/1984 | Canada | 424/66 |
| 0120210 | 10/1984 | European Pat. Off. | 424/66 |
| 0007406 | 1/1982 | Japan | 424/66 |
| 2076289 | 12/1981 | United Kingdom | 424/66 |
| 2144992 | 3/1985 | United Kingdom | 424/66 |

Primary Examiner—Dale R. Ore
Attorney, Agent, or Firm—Kevin B. Clarke

[57] ABSTRACT

Uniform, clear gelled antiperspirant compositions, free of waxes and conventional gelling agents are disclosed. The gel emulsions comprise in combination a volatile silicone fluid, a silicone emulsifier, a destabilizing auxillary emulsifier, water, a non-volatile emollient, a coupling agent, an active antiperspirant component and ancillary agents.

2 Claims, No Drawings

GELLED ANTIPERSPIRANT COMPOSITIONS

This invention relates to cosmetic compositions in gel form, particularly to antiperspirant gels.

BACKGROUND

Antiperspirants and deodorants generally available are in the form of aerosol suspensions, roll-on powders, emulsions or suspensions and solid waxes and suspensions.

Clear antiperspirants have been attempted, but to date, none has reached the market place. It is believed that a clear antiperspirant product which offers efficacy and aesthetic properties equal to or better than products presently available would be well received by the purchasing public.

Clear stick deodorant compositions have been available for some time. The clear sticks are generally produced by using stearate soaps as gelling agents for an alcoholic or gylcolic solution of an anti-microbial agent and a fragrance. These deodorant products offer no antiperspirant protection. To use any of the art recognized antiperspirant active ingredients, which are cationic in nature, in the aforesaid deodorant compositions, is chemically incompatible due to the chemical interaction/inactivation between the antiperspirant active material and the soap.

Geiling may also be achieved through the use of cellulosic or algin derived polymeric materials. Most of these materials are incompatible with electrolytes, i.e., the normally used antiperspirant active ingredients, at the levels required to obtain antiperspirant efficacy. Moreover, the polymer materials are unstable at the low PH, normally encountered in antiperspirant products. For example, polyvalent cations such as $Al^{111}$, among others, will react with the acidic groups on the cellulosic gum resin to form an insoluble salt.

Alginates in the presence of polyvalent cations are precipitated from solution.

Some cellulosic materials, such as hydroxypropylcellulose, among others, are compatible with polyvalent metal salts and have been used in the manufacture of clear lotions. These cellulosic materials, however, must be prepared with a high percentage of water or alcohol in order to insure solubilization of the active ingredient. Such formulations, in addition to a high irritation potential, are tacky and pituitous and low in efficacy when alcohol based, and exhibit tackiness and long drying time when water based.

In order to overcome the lack of compatibility problems, it has been proposed to prepare gels from clear emulsion gel systems, however, due to the high percentage of emulsifiers required, and the nature of the emulsifiers, the products produced have been unaesthetic, slow-drying and retain a high degree of tackiness even after the addition of emollients normally known and utilized to reduce tackiness in antiperspirant products.

Wax and soap-gel sticks are disclosed in various U.S. patents i.e. U.S. Pat. Nos. 4,382,079; 4,414,200; 4,280,994; 4,265,878; 3,259,545; 2,970,083; 2,933,433; 2,900,306 and 2,857,315.

Gelled antiperspirants have been disclosed in U.S. Pat. No. 4,383,988.

SUMMARY

It has now been found that uniform, clear gelled antiperspirant compositions which do not contain waxes nor conventional gelling agents such as soaps, cellulosics or alginates can be prepared. The stable gel emulsions of the present invention are easily applied to the skin and have a smooth, slippery feel yet are fast drying and non-tacky.

The compositions of the present invention are gel emulsions comprising in combination a volatile silicone fluid, a silicone emulsifier, a destabilizing auxillary emulsifier, water, a non-volatile emollient, a coupling agent, an active antiperspirant component and ancillary agents such as perfume, coloring agents etc.

The compositions of the present invention may be prepared by batch process, continuous or semi-continuous process and yield formulations which are stable, highly efficaceous and possess excellent aesthetic qualities.

DETAILED DESCRIPTION

Antiperspirant gel compositions of the present invention do not contain waxes nor conventional gelling agents such as cellulosic, nor gums.

The compositions of the present invention are clear gel emulsions which comprise a unique silicone emulsifier, more precisely, a cyclomethicone-dimethicone copolyol silicone fluid having a viscosity at 25° C. (77° F.) of 600–2000 cps, a specific gravity at 25° C. of about 0.963. Such copolyols are marketed by Dow Corning Corporation under the trademark DOW CORNING 3225C formulation aid.

The silicone emulsifier is present in the compositions of the present invention in amounts ranging from about 10% by weight of the total composition to about 25% by weight of the total composition. The emulsifier is preferably present in amounts of from 15% to 20% by weight of the total composition.

Emolliency and detakifying properties are imparted to the compositions of the present invention by the addition of volatile silicones composed of low molecular weight polydimethylcyclosiloxanes that have been assigned to CTFA name cyclomethicone and are exemplified by the formula:

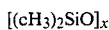

wherein x is an integer of from about 4 to 6. Highly preferred cyclic siloxanes are octamethylcyclotetrasiloxanane (x=4), decamethylcyclopentasiloxane (x=5) and blends of tetramer and pentamer cyclomethicone. Commercial cyclic siloxanes are readily available from manufacturers such as Union Carbide's Trademarked product Volatile Silicone 7207, 7158 and the following Trademarked products of Dow Corning Corporation; Dow Corning 344 Fluid and Dow Corning 345 Fluid; SWS Silicone Corporation, Silicone Fluid F222, F263 and 03314; and G.E. Company SF1173, SF1202.

Desirably the volatile silicones employed in the compositions of the present invention are present in amounts of from about 10% to about 30% by weight of the total composition preferably from 11% to 16% by weight.

A further component of the compositions of the present invention is selected from among the non-volatile emollient materials and mixtures thereof. Such materials in addition to their emollient properties reduce the whitening action of the cyclomethicones. The non-volatile emollient is present in amounts of from about 1% by weight to about 10% by weight of the total composition preferably from about 1% to about 3% by weight.

The non-volatile emollient is selected from among the higher alkyl fatty acid esters and ethers, i.e. those having fatty acid chains of from 10 to 20 carbon atoms, linear silicone fluids, polyalkylene glycols, lanolin, lanolin alcohol and mineral oil. The preferred non-volatiles are selected from isopropyl myristate, isopropyl palmitate, dicapryl adipate, ethyl hexyl isononate, dimethicone or other polydimethylsiloxanes, PPG-20 methyl glucose ether, PPG-15 stearyl ether, mineral oil (and) lanolin alcohol. The non-volatile emollients can be used independently or in combination within the above-noted ranges.

An additional component of the compositions of the present invention is a coupling agent selected from the low molecular weight, i.e. 2 to about 8 carbon atom alcohols and glycols such as ethanol, propylene glycol and polyethylene glycol which is present in amounts of from about 2% by weight of the total composition to about 10%. The coupling agent is preferably present in amounts of from 3.5% to 6.5% by weight.

The active antiperspirant material utilized in the compositions of the present invention is in powder form, or pre-dissolved in water, and may be buffered or unbuffered. Preferred antiperspirant materials are aluminum chlorohydrate, aluminum zirconium trichlorohydrate, tetrachlorohydrate or octachlorohydrate, aluminum sesquichlorohydrate and complexes thereof. The antiperspirant materials are present, in powder form, in amounts of from about 15% by weight of the total composition to about 25% by weight of the total composition preferably from about 20% to about 25% by weight.

Desirably, the compositions of the present invention also contain a auxilliary emulsifier in amounts of from about 0.5% to about 2% by weight of the total composition. Not wishing to be bound by any theory, it is believed that their use in combination with the volatization of the silicones destabilizes the emulsion, thus inhancing the efficacy of the composition.

The balance of the compositions of the present invention, approximately 30% to about 50% by weight, is deionized water. It being understood that additional materials, which are well-known in the antiperspirant art, such as fragrances, bactericides, fungicides, skin treating and conditioning materials etc. may be included in minor amounts in the compositions.

The compositions of the present invention can be prepared by a batch processes among which comprises mixing the antiperspirant active material with water and charging this aqueous phase into the oil-alcohol phase containing the volatile silicone, the silicone emulsifier, the non-volatile emollient, the coupling agent and other non aqueous components and heating the mixture at 25° C. to about 45° C. with agitation until uniform, then homogenizing.

Examples, not to be considered as limiting, of the gel-antiperspirant formulations of the present invention are described below:

| EXAMPLE # | I WT. % | II WT. % | III WT. % | IV WT. % | V WT. % | VI WT. % | VII WT. % | VII WT. % |
|---|---|---|---|---|---|---|---|---|
| Cyclomethicone | 11.00 | 15.50 | 15.50 | 11.00 | 15.50 | 14.50 | 14.50 | 15.50 |
| Cyclomethicone (and) Dimethicone Copolyol | 15.00 | 20.00 | 15.00 | 15.00 | 20.00 | 20.00 | 20.00 | 20.00 |
| P.E.G.-4 Oleate | — | 1.00 | — | — | — | 1.00 | 1.00 | — |
| Laureth-23 | 1.50 | — | 1.50 | 1.50 | 2.00 | — | — | 2.00 |
| Ethanol | 3.50 | 4.00 | 4.00 | 3.50 | — | — | 4.00 | — |
| Propylene Glycol | — | — | — | — | — | 4.00 | — | 6.50 |
| Polydimethyl Siloxane | — | — | — | 2.00 | 2.00 | — | — | 1.00 |
| Isopropyl Myristate | 3.00 | — | — | 3.00 | — | — | — | — |
| Isopropyl Palmitate | — | — | — | — | 1.00 | — | — | 1.00 |
| PPG-15 Stearyl Ether | 2.00 | — | — | — | — | — | — | — |
| Mineral Oil (and) Lanolin Alcohol | — | — | — | — | — | 1.00 | 1.00 | — |
| Aluminum Chlorohydrate | 21.00 | 21.00 | — | — | — | — | — | — |
| Aluminum Zirconium Tetrachlorohydrex Gly | — | — | — | — | — | 21.00 | 21.00 | — |
| Aluminum Zirconium Octachlorohydrex Gly | — | — | 21.00 | 21.00 | 22.00 | — | — | 22.00 |
| Water | 42.50 | 38.00 | 42.50 | 42.50 | 37.00 | 38.00 | 38.00 | 31.50 |
| Perfume | 0.50 | 0.50 | 0.50 | 0.50 | 0.50 | 0.50 | 0.50 | 0.50 |

What is claimed is:

1. A clear gelled antiperspirant composition free of waxes and gelling agents containing:
   (a) from about 10% to about 25% by weight of a cyclomethicone-dimethicone copolysilicone fluid having a viscosity of 25 C. of 600–2000 cps;
   (b) from about 10% to about 30% by weight of a volatile polydimethylcyclosiloxane exemplified by the formula $[CCH_3)_2SiO]_x$ wherein x is an integer of from 4 to 6;
   (c) from about 1% to about 10% by weight of a non-volatile emollient material selected from the group consisting of fatty acid esters, fatty acid ethers, linear silicone fluids, polyalkylene glycols, lanolin, lanolin alcohol, mineral oil and mixtures thereof;
   (d) from about 2% to about 10% by weight of a coupling agent selected from the group consisting of low molecular weight alcohols and glycols;
   (e) from about 15% to about 25% by weight of an active antiperspirant material selected from the group consisting of aluminum chlorohydrates, aluminum zirconium chlorohydrates and complexes thereof.

2. Compositions as claimed in claim 1 which additionally contain one or more fragrances, bactericides, or fungicides.

* * * * *